US006440444B2

(12) United States Patent
Boyce et al.

(10) Patent No.: US 6,440,444 B2
(45) **Date of Patent: *Aug. 27, 2002**

(54) LOAD BEARING OSTEOIMPLANT AND METHOD OF REPAIRING BONE USING THE SAME

(75) Inventors: Todd M. Boyce, Aberdeen; Lawrence A. Shimp, Morganville; Albert Manrique, Manalapan, all of NJ (US)

(73) Assignee: Osteotech, Inc., Eatontown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/911,562

(22) Filed: Jul. 24, 2001

Related U.S. Application Data

(63) Continuation of application No. 09/256,447, filed on Feb. 23, 1999, now Pat. No. 6,294,187.

(51) Int. Cl.[7] .............................. A61F 13/00; A61F 2/00

(52) U.S. Cl. ........................ 424/422; 424/443; 424/484; 424/623; 424/16

(58) Field of Search ................................. 424/422, 423, 424/484; 623/16

(56) References Cited

U.S. PATENT DOCUMENTS 6,294,187 B1 * 9/2001 Boyce et al.

* cited by examiner

*Primary Examiner*—Thurman K. Page
*Assistant Examiner*—Isis Ghali
(74) *Attorney, Agent, or Firm*—Dilworth & Barrese, LLP

(57) ABSTRACT

A load-bearing osteoimplant, method of making the osteoimplant and method for repairing bone using the osteoimplant are provided. The osteoimplant comprises a shaped, compressed composition of bone particles. The osteoimplant possesses a bulk density of greater than about 0.7 $g/cm^3$ and a wet compressive strength of at least about 3 MPa.

30 Claims, 9 Drawing Sheets

LOAD BEARING OSTEOIMPLANT AND METHOD OF REPAIRING BONE USING THE SAME

CROSS REFERENCE TO RELATED APPLICATION

This application is a continuation of U.S. application Ser. No. 09/256,447, filed Feb. 23, 1999, now U.S. Pat. No. 09/256,447.

FIELD OF THE INVENTION

The present invention relates to an osteoimplant for use in the repair, replacement and/or augmentation of various portions of animal or human skeletal systems, to a method for manufacturing the osteoimplant and to a method of using the osteoimplant. More particularly, this invention relates to an osteogenic osteoimplant which provides mechanical or structural support to a bone repair site.

BACKGROUND OF THE INVENTION

Shaped or cut bone segments have been used extensively to solve various medical problems in human and animal orthopaedic surgical practice, and their application has also extended to the field of cosmetic and reconstructive surgery, dental reconstructive surgery, and other medical fields involving surgery of hard tissues. The use of autograft bone (where the patient provides the source), allograft bone (where another individual of the same species provides the source) or xenograft bone (where another individual of a different species provides the source) is well known in both human and veterinary medicine. In particular, transplanted bone is known to provide support, promote healing, fill bony cavities, separate bony elements (such as vertebral bodies), promote fusion (where bones are induced to grow together into a single, solid mass), or stabilize the sites of fractures. More recently, processed bone has been developed into shapes for use in new surgical applications, or as new materials for implants that were historically made of non-biologically derived materials.

Bone grafting applications are differentiated by the requirements of the skeletal site. Certain applications require a "structural graft" in which one role of the graft is to provide mechanical or structural support to the site. Such grafts contain a substantial portion of mineralized bone tissue to provide the strength needed for load-bearing. The graft may also have beneficial biological properties, such as incorporation into the skeleton, osteoinduction, osteoconduction, or angiogenesis.

Structural grafts are conventionally made by processing, and then cutting or otherwise shaping cortical bones collected for transplant purposes. The range of bone grafts that might be thus prepared is limited by the size and shape limitations of the bone TISSUE from which the bone graft originated. Certain clinically desirable shapes and sizes of grafts may thus be unattainable by the cutting and shaping processes, due to the dimensional limitations of the bone. For some shapes they may also be available only in limited amounts, due to the large variations inherent in the human or animal donor source populations.

Many structural allografts are never fully incorporated by remodeling and replacement with host tissue due, in part, to the difficulty with which the host's blood supply may penetrate cortical bone, and partly to the poor osteoinductivity of nondemineralized bone. To the extent that the implant is incorporated and replaced by living host bone tissue, the body can then recognize and repair damage, thus eliminating failure by fatigue. In applications where the mechanical load-bearing requirements of the graft are challenging, lack of replacement by host bone tissue may compromise the graft by subjecting it to repeated loading and cumulative unrepaired damage (mechanical fatigue) within the implant material. Thus, it is highly desirable that the graft have the capacity to support load initially, and be capable of gradually transferring this load to the host bone tissue as it remodels the implant.

SUMMARY OF THE INVENTION

It is an object of the present invention to provide an osteoimplant possessing sufficient strength in a body fluid environment to enable the osteoimplant to bear loads.

It is a further object of the present invention to provide a load-bearing osteoimplant which contains pores or cavities which permit the osteoimplant to be properly revascularized and incorporated by the host.

It is yet a further object of the present invention to provide a load-bearing osteoimplant which is osteogenic and thereby promotes new host bone tissue formation within and around the osteoimplant.

It is yet an even further object of the invention to provide a load-bearing osteoimplant which supports load initially and is capable of gradually transferring this load to the host bone tissue as it remodels the osteoimplant.

It is yet an even further object of the invention to provide a method for fabricating an osteoimplant which meets the foregoing objectives.

It is yet an even further object of the present invention to provide a method which enables the fabrication of osteoimplants of any size and/or shape.

It is yet an even further object of the present invention to provide a method for preparing osteoimplants which is not limited by constraints imposed by the shape and size of the original bone tissue from which the osteoimplants are derived.

These and further objects of the invention are obtained by a load-bearing osteoimplant which comprises a shaped, compressed composition of bone particles. The osteoimplant possesses a bulk density of greater than about 0.7 g/cm$^3$ and a wet compressive strength of at least about 3 MPa. The osteoimplant of this invention is fabricated by the method which comprises providing a composition comprising bone particles optionally in combination with one or more biocompatible components and applying compressive force of greater than about 1000 psi to the composition to provide a load-bearing osteoimplant.

The bone particles utilized in the fabrication of the osteoimplant of this invention are selected from the group consisting of nondemineralized bone particles, demineralized bone particles, and combinations thereof. The bone particles are remodeled and replaced by new host bone as incorporation of the osteoimplant progresses in vivo. As described more fully hereinbelow, bone particles can be fully demineralized by removing substantially all of the inorganic mineral content of the bone particles, can be partially demineralized by removing a significant amount, but less than all, of the inorganic mineral content of the bone particles, or can be only superficially demineralized by removing a minor amount of the inorganic mineral content of the bone particles.

The term "demineralized" as applied to the bone particles utilized in the practice of the present invention is intended to cover all bone particles which have had some portion of their original mineral content removed by a demineralization process.

Nondemineralized bone particles provide strength to the osteoimplant and allow it to initially support load. Demineralized bone particles induce new bone formation at the site of the demineralized bone and permit adjustment of the overall mechanical properties of the osteoimplant. The osteoimplant of this invention optionally includes additional biocompatible component(s) such as wetting agents, biocompatible binders, fillers, fibers, plasticizers, biostatic/biocidal agents, surface active agents, bioactive agents, and the like.

The term "osteoimplant" herein is utilized in its broadest sense and is not intended to be limited to any particular shapes, sizes, configurations or applications.

The term "shaped" as applied to the osteoimplant herein refers to a determined or regular form or configuration, in contrast to an indeterminate or vague form or configuration (as in the case of a limp or other solid mass of no special form) and is characteristic of such materials as sheets, plates, disks, cores, pins, screws, tubes, teeth, bones, portion of bone, wedges, cylinders, threaded cylinders, and the like.

The phrase "wet compressive strength" as utilized herein refers to the compressive strength of the osteoimplant after the osteoimplant has been immersed in physiological saline (water containing 0.9 g NaCl/100 ml water) for a minimum of 12 hours and a maximum of 24 hours. Compressive strength is a well known measurement of mechanical strength and is measured using the procedure described herein.

The term "osteogenic" as applied to the osteoimplant of this invention shall be understood as referring to the ability of the osteoimplant to enhance or accelerate the ingrowth of new bone tissue by one or more mechanisms such as osteogenesis, osteoconduction and/or osteoinduction.

The term "incorporation" utilized herein refers to the biological mechanism whereby host tissue gradually removes portions of the osteoimplant of the invention and replaces those removed portions with native host bone tissue while maintaining strength. This phenomenon is also known in the scientific literature as "creeping substitution". The term "incorporation" utilized herein shall be understood as embracing what is known by those skilled in the art as "creeping substitution".

BRIEF DESCRIPTION OF THE DRAWINGS

Various embodiments are described below with reference to the drawings wherein.

DESCRIPTION OF THE PREFERRED EMBODIMENTS

Figure 1A:
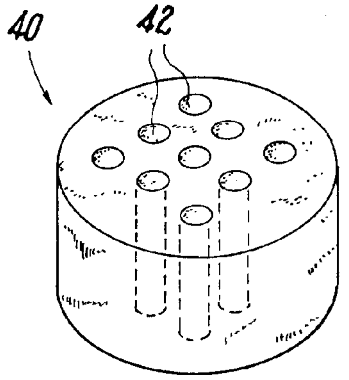
FIGS. 1*a*–*h* show various configurations of an osteoimplant of the present invention.
Figure 1B:
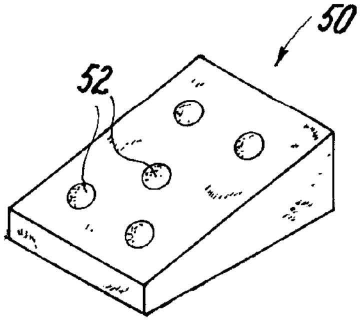
Figure 1C:
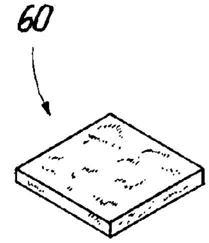

The load-bearing osteoimplant of the present invention is produced by providing a composition comprising bone particles optionally in combination with one or more biocompatible components, and thereafter applying compressive force of at least about 1000 psi to the composition to provide a load-bearing osteoimplant. The osteoimplant fabricated in accordance with the invention possesses a bulk density of at least about 0.7 g/cm$^3$ and a wet compressive strength of at least about 3 MPa. In accordance with further embodiments of the invention, the bone particle-containing composition can be heated, lyophilized and/or cross-linked either before, during or after the step of applying a compressive force to the bone particle-containing composition.

The bone particles employed in the preparation of the bone particle-containing composition can be obtained from cortical, cancellous and/or corticocancellous bone which may be of autogenous, allogenic and/or xenogeneic origin. Preferably, the bone particles are obtained from cortical bone of allogenic origin. Porcine and bovine bone are particularly advantageous types of xenogeneic bone tissue which can be used individually or in combination as sources for the bone particles. Particles are formed by milling whole bone to produce fibers, chipping whole bone, cutting whole bone, fracturing whole bone in liquid nitrogen, or otherwise disintegrating the bone tissue. Particles can optionally be sieved to produce those of a specific size.

The bone particles employed in the composition can be powdered bone particles possessing a wide range of particle sizes ranging from relatively fine powders to coarse grains and even larger chips. Thus, e.g., powdered bone particles can range in average particle size from about 0.05 to about 1.2 cm and preferably from about 0.1 to about 1 cm and possess an average median length to median thickness ratio of from about 1:1 to about 3:1. If desired, powdered bone particles can be graded into different sizes to reduce or eliminate any less desirable size(s) of particles which may be present.

Alternatively, or in combination with the aforementioned bone powder, bone particles generally characterized as elongate and possessing relatively high median length to median thickness ratios can be utilized herein. Such elongate particles can be readily obtained by any one of several methods, e.g., by milling or shaving the surface of an entire bone or relatively large section of bone. Employing a milling technique, one can obtain a mass of elongate bone particles containing at least about 60 weight percent, preferably at least about 70 weight percent, and most preferably at least about 80 weight percent of elongate bone particles possessing a median length of from about 2 to about 200 mm or more and preferably from about 10 to about 100 mm, a median thickness of from about 0.05 to about 2 mm, and preferably from about 0.2 to about 1 mm and a median width of from about 1 mm to about 20 mm, and preferably from about 2 to about 5 mm. These elongate bone particles can possess a median length to median thickness ratio of at least about 50:1 up to about 500:1 or more, and preferably from about 50:1 to about 100:1 and a median length to median width ratio of from about 10:1 and about 200:1, and preferably from about 50:1 to about 100:1. Another procedure for obtaining elongate bone particles, particularly useful for pieces of bone of up to about 100 mm in length, is the bone processing mill described in commonly assigned U.S. Pat. No. 5,607,269. Use of this bone mill results in the production of long, thin strips which quickly curl lengthwise to provide tubular-like bone particles. If desired, elongate bone particles can be graded into different sizes to reduce or eliminate any less desirable size(s) of particles which may be present. In overall appearance, elongate bone particles can be described as filaments, fibers, threads, slender or narrow strips, etc.

Preferably, at least about 60 weight percent, more preferably at least about 75 weight percent, and most preferably at least about 90 weight percent of the bone particles utilized in the preparation of the bone particle-containing composition herein are elongate. It has been observed that elongate bone particles provide an osteoimplant possessing particularly good compressive strength.

The bone particles are optionally demineralized in accordance with known and conventional procedures in order to reduce their inorganic mineral content. Demineralization methods remove the inorganic mineral component of bone by employing acid solutions. Such methods are well known in the art, see for example, Reddi et al., *Proc. Nat. Acad. Sci.* 69, pp1601–1605 (1972), incorporated herein by reference herein. The strength of the acid solution, the shape of the bone particles and the duration of the demineralization treatment will determine the extent of demineralization. Reference in this regard may be made to Lewandrowski et al., *J. Biomed Materials Res,* 31, pp 365–372 (1996), also incorporated herein by reference.

In a preferred demineralization procedure, the bone particles are subjected to a defatting/disinfecting step which is followed by an acid demineralization step. A preferred defatting/disinfectant solution is an aqueous solution of ethanol, the ethanol being a good solvent for lipids and the water being a good hydrophilic carrier to enable the solution to penetrate more deeply into the bone particles. The aqueous ethanol solution also disinfects the bone by killing vegetative microorganisms and viruses. Ordinarily, at least about 10 to about 40 percent by weight of water (i.e., about 60 to about 90 weight percent of defatting agent such as alcohol) should be present in the defatting disinfecting solution to produce optimal lipid removal and disinfection within the shortest period of time. The preferred concentration range of the defatting solution is from about 60 to about 85 weight percent alcohol and most preferably about 70 weight percent alcohol. Following defatting, the bone particles are immersed in acid over time to effect their demineralization. Acids which can be employed in this step include inorganic acids such as hydrochloric acid and organic acids such as peracetic acid. After acid treatment, the demineralized bone particles are rinsed with sterile water to remove residual amounts of acid and thereby raise the pH. Where elongate bone particles are employed, some entanglement of the wet demineralized bone particles will result. The wet demineralized bone particles can then be immediately shaped into any desired configuration or stored under aseptic conditions, advantageously in a lyophilized state, for processing at a later time. As an alternative to aseptic processing and storage, the particles can be shaped into a desired configuration and sterilized using known methods.

As utilized herein, the phrase "superficially demineralized" as applied to the bone particles refers to bone particles possessing at least about 90 weight percent of their original inorganic mineral content. The phrase "partially demineralized" as applied to the bone particles refers to bone particles possessing from about 8 to about 90 weight percent of their original inorganic mineral content, and the phrase "fully demineralized" as applied to the bone particles refers to bone particles possessing less than about 8, preferably less than about 1, weight percent of their original inorganic mineral content. The unmodified term "demineralized" as applied to the bone particles is intended to cover any one or combination of the foregoing types of demineralized bone particles.

Mixtures or combinations of one or more of the foregoing types of bone particles can be employed. For example, one or more of the foregoing types of demineralized bone particles can be employed in combination with nondemineralized bone particles, i.e., bone particles that have not been subjected to a demineralization process.

Nondemineralized bone particles possess an initial and ongoing mechanical role, and later a biological role, in the osteoimplant of this invention. Nondemineralized bone particles act as a stiffener, providing strength to the osteoimplant and enhancing its ability to support load. These bone particles also play a biological role in bringing about new bone ingrowth by the process known as osteoconduction. Thus, these bone particles are gradually remodeled and replaced by new host bone as incorporation of the osteoimplant progresses over time. The use of nondemineralized bone particles is highly preferred, albeit not essential, in the fabrication of the osteoimplant of the present invention.

Demineralized bone particles likewise possess an initial and ongoing mechanical role, and later a biological role, in the osteoimplant of this invention. Superficial or partial demineralization produces particles containing a mineralized core. Particles of this type actually can contribute to the strength of the osteoimplant, through their mineralized core. These particles also play a biological role in bringing about new bone ingrowth by the process known as osteoinduction. Full demineralization produces particles in which nearly all of the mineral content has been removed from the particles. Particles treated in this way do not directly contribute to the strength of the osteoimplant; however, they do contribute to the osteoinductivity of the osteoimplant and provide a coherency or binding effect.

When prepared from bone particles that are almost exclusively nondemineralized and/or superficially demineralized the osteoimplant herein will tend to possess a fairly high compressive strength, e.g., one approaching and even exceeding that of natural bone. Accordingly, when an osteoimplant exhibiting a wet compressive strength of on the order of from about 20 to about 200 MPa, is desired, a predominant amount of nondemineralized bone particles and/or superficially demineralized bone particles can be advantageously employed. In order to lower the compressive strength of the osteoimplant, a quantity of partially or fully demineralized bone particles can be employed in combination with nondemineralized bone particles or superficially demineralized bone particles. Thus, the use of various types of bone particles can be used to control the overall mechanical and biological properties, i.e., the strength, osteoconductivity and/or osteoinductivity, etc., of the osteoimplant. The differential in compressive strength, osteogenicity and other properties between partially and/or fully demineralized bone particles on the one hand and non-demineralized and/or superficially demineralized bone particles on the other hand can be exploited. For example, nondemineralized and/or superficially demineralized bone particles can be concentrated in that region of the osteoimplant which will be directly subjected to applied load upon implantation.

In one embodiment, where the composition is compressed in a mold, e.g., a cylindrical press-mold, the walls of the mold can be coated with a slurry or paste containing partially and/or fully demineralized bone particles followed by addition of a slurry or paste containing nondemineralized and/or superficially demineralized bone particles (or vice versa) to provide an osteoimplant which contains at least one discrete region, e.g., an outer surface, composed of partially and/or fully demineralized bone particles and at least one discrete region, e.g., a core, composed of nondemineralized and/or superficially demineralized bone particles.

The amount of each individual type of bone particle employed can vary widely depending on the mechanical and biological properties desired. Thus, e.g., the weight ratio of nondemineralized to demineralized bone particles can broadly range from about 20:1 to about 1:20 and the weight ratio of superficially and/or partially demineralized bone particles to fully demineralized bone particles can broadly range from about 20:1 to about 1:20. Suitable amounts can be readily determined by those skilled in the art on a case-by-case basis by routine experimentation.

If desired, the bone particles can be modified in one or more ways, e.g., their protein content can be augmented or modified as described in U.S. Pat. Nos. 4,743,259 and 4,902,296, the contents of which are incorporated by reference herein.

The bone particle-containing composition fabricated in accordance with this disclosure will typically possess a bone particle content ranging from about 5 to about 100 weight percent, preferably from about 40 to about 99 weight percent, and more preferably from about 50 to about 95 weight percent, based on the weight of the entire composition calculated prior to compression of the composition.

The bone particles can be combined with one or more biocompatible components such as wetting agents, biocompatible binders, fillers, fibers, plasticizers, biostatic/biocidal agents, surface active agents, bioactive agents, and the like, prior to, during, or after compressing the bone particle-containing composition. One or more of such components can be combined with the bone particles by any suitable means, e.g., by soaking or immersing the bone particles in a solution or dispersion of the desired component, by physically admixing the bone particles and the desired component, and the like.

Suitable wetting agents include biocompatible liquids such as water, organic protic solvent, aqueous solution such as physiological saline, concentrated saline solutions, sugar solutions, ionic solutions of any kind, and liquid polyhydroxy compounds such as glycerol and glycerol esters, and mixtures thereof. The use of wetting agents in general is preferred in the practice of the present invention, as they improve handling of bone particles. When employed, wetting agents will typically represent from about 20 to about 80 weight percent of the bone particle-containing composition, calculated prior to compression of the composition. Certain wetting agents such as water can be advantageously removed from the osteoimplant, e.g., by heating and lyophilizing the osteoimplant.

Suitable biocompatible binders include biological adhesives such as fibrin glue, fibrinogen, thrombin, mussel adhesive protein, silk, elastin, collagen, casein, gelatin, albumin, keratin, chitin or chitosan; cyanoacrylates; epoxy-based compounds; dental resin sealants; bioactive glass ceramics (such as apatite-wollastonite), dental resin cements; glass ionomer cements (such as Ionocap® and Inocem® available from lonos Medizinische Produkte GmbH, Greisberg, Germany); gelatin-resorcinol-formaldehyde glues; collagen-based glues; cellulosics such as ethyl cellulose; bioabsorbable polymers such as starches, polylactic acid, polyglycolic acid, polylactic-co-glycolic acid, polydioxanone, polycaprolactone, polycarbonates, polyorthoesters, polyamino acids, polyanhydrides, polyhydroxybutyrate, polyhyroxyvalyrate, poly (propylene glycol-co-fumaric acid), tyrosine-based polycarbonates, pharmaceutical tablet binders (such as Eudragit® binders available from Hüils America, Inc.), polyvinylpyrrolidone, cellulose, ethyl cellulose, micro-crystalline cellulose and blends thereof; starch ethylenevinyl alcohols, polycyanoacrylates; polyphosphazenes; nonbioabsorbable polymers such as polyacrylate, polymethyl methacrylate, polytetrafluoroethylene, polyurethane and polyamide; etc. Preferred binders are polyhydroxybutyrate, polyhydroxyvalerate and tyrosine-based polycarbonates. When employed, binders will typically represent from about 5 to about 70 weight percent of the bone particle-containing composition, calculated prior to compression of the composition.

The use of biocompatible binder as biocompatible component is particularly preferred in the practice of the present invention. Biocompatible binder acts as a matrix which binds the bone particles, thus providing coherency in a fluid environment and also improving the mechanical strength of the osteoimplant.

Suitable fillers include graphite, pyrolytic carbon, bioceramics, bone powder, demineralized bone powder, anorganic bone (i.e., bone mineral only, with the organic constituents removed), dentin tooth enamel, aragonite, calcite, nacre, amorphous calcium phosphate, hydroxyapatite, tricalcium phosphate, Bioglass® and other calcium phosphate materials, calcium salts, etc. Preferred fillers are demineralized bone powder and hydroxyapatite. When employed, filler will typically represent from about 5 to about 80 weight percent of the bone particle-containing composition, calculated prior to compression of the composition.

Suitable fibers include carbon fibers, collagen fibers, tendon or ligament derived fibers, keratin, cellulose, hydroxyapatite and other calcium phosphate fibers. When employed, fiber will typically represent from about 5 to about 75 weight percent of the bone particle-containing composition, calculated prior to compression of the composition.

Suitable plasticizers include liquid polyhydroxy compounds such as glycerol, monoacetin, diacetin, etc. Glycerol and aqueous solutions of glycerol are preferred. When employed, plasticizer will typically represent from about 20 to about 80 weight percent of the bone particle-containing composition, calculated prior to compression of the composition.

Suitable biostatic/biocidal agents include antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamicin, povidone, sugars, mucopolysaccharides, etc. Preferred biostatic/biocidal agents are antibiotics. When employed, biostatic/biocidal agent will typically represent from about 10 to about 95 weight percent of the bone particle-containing composition, calculated prior to compression of the composition.

Suitable surface active agents include the biocompatible nonionic, cationic, anionic and amphoteric surfactants. Preferred surface active agents are the nonionic surfactants. When employed, surface active agent will typically represent from about 1 to about 80 weight percent of the bone particle-containing composition, calculated prior to compression of the composition.

Any of a variety of bioactive substances can be incorporated in, or associated with, the bone particles. Thus, one or more bioactive substances can be combined with the bone particles by soaking or immersing the bone particles in a solution or dispersion of the desired bioactive substance(s). Bioactive substances include physiologically or pharmacologically active substances that act locally or systemically in the host.

Bioactive substances which can be readily combined with the bone particles include, e.g., collagen, insoluble collagen derivatives, etc., and soluble solids and/or liquids dissolved therein; antiviricides, particularly those effective against HIV and hepatitis; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamicin, etc.; biocidal/biostatic sugars such as dextran, glucose, etc.; amino acids; peptides; vitamins; inorganic elements; co-factors for protein synthesis; hormones; endocrine tissue or tissue fragments; synthesizers; enzymes such as collagenase, peptidases, oxidases, etc.; polymer cell scaffolds with parenchymal cells; angiogenic agents and polymeric carriers containing such agents; collagen lattices; antigenic agents; cytoskeletal agents; cartilage fragments; living cells such as chondrocytes, bone marrow cells, mesenchymal stem cells, natural extracts, genetically engineered living cells or otherwise modified living cells; DNA delivered by plasmid or viral vectors; tissue transplants; demineralized bone powder; autogenous tissues such as blood, serum, soft tissue, bone marrow, etc.; bioadhesives, bone morphogenic proteins (BMPs); osteoinductive factor; fibronectin (FN); endothelial cell growth factor (ECGF); cementum attachment extracts (CAE); ketanserin; human growth hormone (HGH); animal growth hormones; epidermal growth factor (EGF); interleukin-1 (IL-1); human alpha thrombin; transforming growth factor (TGF-beta); insulin-like growth factor (IGF-1); platelet derived growth factors (PDGF); fibroblast growth factors (FGF, bFGF, etc.); periodontal ligament chemotactic factor (PDLGF); somatotropin; bone digestors; antitumor agents; immuno-suppressants; permeation enhancers, e.g., fatty acid esters such as laureate, myristate and stearate monoesters of polyethylene glycol, enamine derivatives, alpha-keto aldehydes, etc.; and nucleic acids. Preferred bioactive substances are currently bone morphogenic proteins and DNA delivered by plasmid or viral vector. When employed, bioactive substance will typically represent from about 0.1 to about 20 weight percent of the bone particle-containing composition, calculated prior to compression of the composition.

It will be understood by those skilled in the art that the foregoing biocompatible components are not intended to be exhaustive and that other biocompatible components may be admixed with bone particles within the practice of the present invention.

The total amount of such optionally added biocompatible substances will typically range from about 0 to about 95, preferably from about 1 to about 60, more preferably from about 5 to about 50, weight percent of the bone particle-containing composition, based on the weight of the entire composition prior to compression of the composition, with optimum levels being readily determined in a specific case by routine experimentation.

One method of fabricating the bone particle-containing composition which can be advantageously utilized herein involves wetting a quantity of bone particles, of which at least about 60 weight percent preferably constitute elongate bone particles, with a wetting agent as described above to form a composition having the consistency of a slurry or paste. Optionally, the wetting agent can comprise dissolved or admixed therein one or more biocompatible substances such as biocompatible binders, fillers, plasticizers, biostatic/biocidal agents, surface active agents, bioactive substances, etc., as previously described.

Preferred wetting agents for forming the slurry or paste of bone particles include water, liquid polyhydroxy compounds and their esters, and polyhydroxy compounds in combination with water and/or surface active agents, e.g., the Pluronics® series of nonionic surfactants. Water is the most preferred wetting agent for utilization herein. The preferred polyhydroxy compounds possess up to about 12 carbon atoms and, where their esters are concerned, are preferably the monoesters and diesters. Specific polyhydroxy compounds of the foregoing type include glycerol and its monoesters and diesters derived from low molecular weight carboxylic acids, e.g., monoacetin and diacetin (respectively, glycerol monoacetate and glycerol diacetate), ethylene glycol, diethylene glycol, triethylene glycol, 1,2-propanediol, trimethylolethane, trimethylolpropane, pentaerythritol, sorbitol, and the like. Of these, glycerol is especially preferred as it improves the handling characteristics of the bone particles wetted therewith and is biocompatible and easily metabolized. Mixtures of polyhydroxy compounds or esters, e.g., sorbitol dissolved in glycerol, glycerol combined with monoacetin and/or diacetin, etc., are also useful. Where elongate bone particles are employed, some entanglement of the wet bone particles will result. Preferably, excess liquid can be removed from the slurry or paste, e.g., by applying the slurry or paste to a form such as a flat sheet, mesh screen or three-dimensional mold and draining away excess liquid.

Where, in a particular composition, the bone particles have a tendency to quickly or prematurely separate or to otherwise settle out from the slurry or paste such that application of a fairly homogeneous composition is rendered difficult or inconvenient, it can be advantageous to include within the composition a substance whose thixotropic characteristics prevent or reduce this tendency. Thus, e.g., where the wetting agent is water and/or glycerol and separation of bone particles occurs to an excessive extent where a particular application is concerned, a thickener such as a solution of polyvinyl alcohol, polyvinylpyrrolidone, cellulosic ester such as hydroxypropyl methylcellulose, carboxy methylcellulose, pectin, xanthan gum, food-grade texturizing agent, gelatin, dextran, collagen, starch, hydrolyzed polyacrylonitrile, hydrolyzed polyacrylamide, polyelectrolyte such as polyacrylic acid salt, hydrogels, chitosan, other materials that can suspend particles, etc., can be combined with the wetting agent in an amount sufficient to significantly improve the suspension-keeping characteristics of the composition.

After production of the bone particle-containing composition, the composition is subjected to a compressive force of at least about 1,000 psi to produce the osteoimplant of this invention. Typically, compressive forces of from about 2,500 to about 60,000 psi can be employed with particularly good effect, with compressive forces of from about 2,500 to about 20,000 psi presently being preferred. The compression step will typically be conducted for a period of time ranging from about 0.1 to about 180 hours, preferably from about 4 to about 72 hours. The resulting osteoimplant possesses a bulk density (measured by dividing the weight of the osteoimplant by its volume) of at least about 0.7 g/cm$^3$, preferably at least about 1.0 g/cm$^3$. After being immersed in physiological saline for 12–24 hours, the osteoimplant of this invention possesses a wet compressive strength (as measured by the method described hereinbelow) of at least about 3 MPa. Typically, the wet compressive strength of the osteoimplant substantially exceeds 3 MPa. In most cases (and especially where a predominant amount of nondemineralized elongate bone particles are utilized in the fabrication of the osteoimplant), the inventors have found that wet compressive strength normally exceeds about 15 MPa and typically ranges from about 15 to about 100 MPA. The wet compressive strength of the osteoimplant of this invention allows the osteoimplant to provide significant mechanical or structural support to a bone repair site in a body fluid environment over an extended period of time in vivo.

To effect compression of the composition, the composition can be placed in a mold possessing any suitable or desired shape or configuration and compressed in a press, e.g., a Carver® manual press.

Figure 12A:
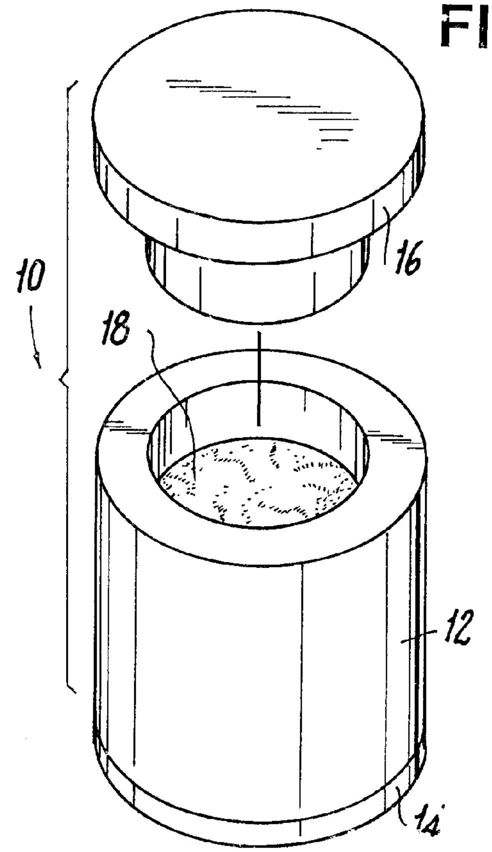
FIGS. 12*a* and 12*b* show a cylindrical press-mold which can be utilized in the fabrication of the osteoimplant of the invention.
Figure 12B:
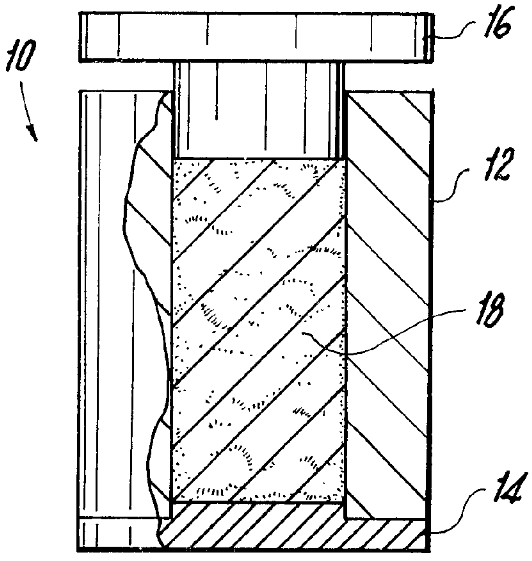
Figure 14:
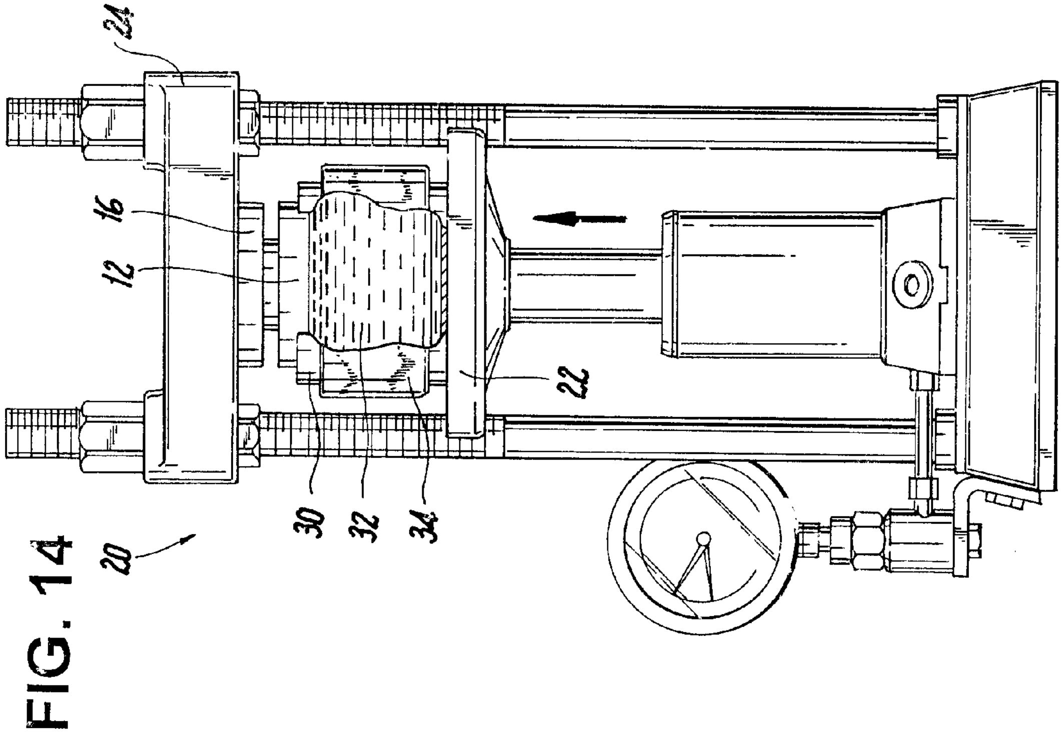
FIG. 14 shows a press and heating apparatus which can be utilized in the fabrication of the osteoimplant of the invention.
Figure 13:
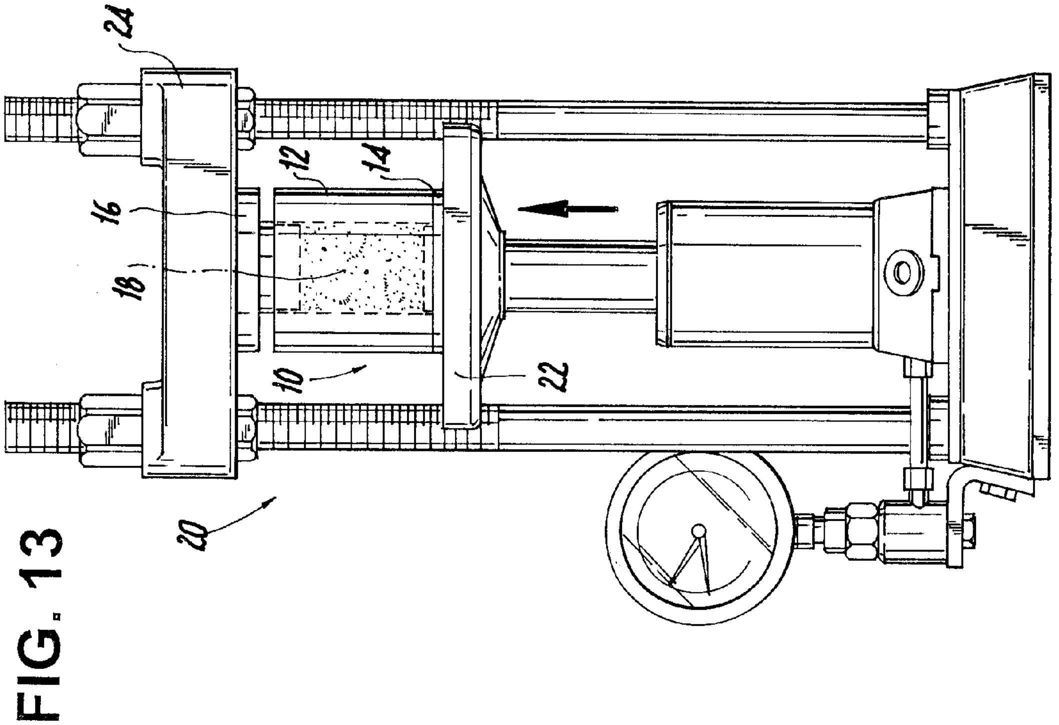
FIG. 13 shows a press which can be utilized in the fabrication of the osteoimplant of the invention.

FIGS. 12*a* and 12*b* depict a cylindrical press-mold 10 which is suitable for use in the present invention. Mold 10 consists of three parts, a hollow cylinder 12, an end cap 14 and a plunger 16. Mold 10 is assembled by placing hollow cylinder 10 on top of end cap 12. The interior of hollow cylinder 12 is then filled with the bone particle-containing composition described herein, shown at 18. Thereafter, plunger 16 is placed on top of cylinder 10 which has been filled with bone particle-containing composition 18. As shown best in FIG. 12*b*, bone particle-containing composition 18 is filled to a height inside cylinder 12 which results in plunger 16 coming to a rest on composition 18 instead of cylinder 12. As shown in FIG. 13, mold 10 is placed inside a manual hydraulic press, generally depicted at 20. Press 20 is equipped with two plates 22 and 24. Plate 24 remains stationary while plate 22 moves in an upward direction as indicated by the arrow in FIG. 13. Movement of plate 22 is hydraulically controlled by means of a handle or other means (not shown) which is operated by the user. As plate 22 moves upward, plunger 16 is forced against plate 24 and moves downward to apply compressive force against composition 18 inside mold 10.

The osteoimplant produced by the method of this invention can be described as a hard, chalk-like material. The osteoimplant may possess tiny pores or cavities which permit the osteoimplant to be properly revascularized and incorporated by the host. It can be easily shaped or machined into any of a wide variety of configurations. In accordance with a preferred embodiment, the osteoimplant is provided with macroporosity, i.e., holes, which enhance blood flow through the osteoimplant or can be filled with a medically useful substance (such as Grafton® putty available from Osteotech Inc., Eatontown, N.J.). Such macroporosity can be provided, e.g., by drilling or by using a mold which possesses spikes therein.

Before, during or after application of compressive force to the bone particle-containing composition, the composition can be subjected to an additional operation selected from heating, lyophilizing and cross-linking to further enhance the mechanical and/or biological properties of the osteoimplant. Incorporation of biocompatible component(s), if any, to the composition can precede or come after the step(s) of subjecting the composition to such additional operation(s).

In accordance with a preferred embodiment, the composition is heated during or after the compression step. The composition can be heated at a suitable temperature, e.g., one ranging from about 30° to about 70° C., preferably from about 40° to about 50° C., for 1 to 72 hours preferably 24 to 48 hours. A presently preferred mode of heating involves placing the bone particle-containing composition in a mold and immersing the mold in a heated biocompatible liquid, e.g., water, glycerol, solution of glycerol and water, ionic solutions of any kind, saline, concentrated saline, etc., such that the liquid can communicate with the composition being compressed. Concentrated saline is preferred. The composition inside the mold is compressed to provide an osteoimplant in accordance with the present invention. As shown in FIG. 13, mold 10 is placed in container 30 which is filled with biocompatible liquid 32. Surrounding container 30 is a heat tape 34 which contains electric heating elements (not shown) which are controlled by an electrostat (not shown). By raising the temperature of biocompatible liquid 32, heat is transferred to the composition (not shown) inside mold 10. As plate 22 moves upward, plunger 16 is compressed against plate 24 and exerts downward compressive force against the composition. While not wishing to be bound by theory, it is believed that biocompatible liquid 32 actually enters mold 10 through seams formed by the connection between end cap 14 and cylinder 12 and contacts the composition. It has been discovered that this mode of heating provides osteoimplants possessing particularly good strength characteristics.

The osteoimplant can be lyophilized, advantageously after the bone particle-containing composition has been compressed in accordance with this disclosure, under conditions that are well known in the art, e.g., a shelf temperature of from about −20° to about −55° C., a vacuum of from about 150 to about 100 mTorr for a period of time ranging from about 4 to about 48 hours.

Crosslinking can be performed in order to improve the strength of the osteoimplant. Crosslinking of the bone particle-containing composition can be effected by a variety of known methods including chemical reaction, the application of energy such as radiant energy, which includes irradiation by UV light or microwave energy, drying and/or heating and dye-mediated photo-oxidation; dehydrothermal treatment in which water is slowly removed while the bone particles are subjected to a vacuum; and, enzymatic treatment to form chemical linkages at any collagen-collagen interface. The preferred method of forming chemical linkages is by chemical reaction.

Chemical crosslinking agents include those that contain bifunctional or multifunctional reactive groups, and which react with surface-exposed collagen of adjacent bone particles within the bone particle-containing composition. By reacting with multiple functional groups on the same or different collagen molecules, the chemical crosslinking agent increases the mechanical strength of the osteoimplant.

Chemical crosslinking involves exposing the bone particles presenting surface-exposed collagen to the chemical crosslinking agent, either by contacting bone particles with a solution of the chemical crosslinking agent, or by exposing bone particles to the vapors of the chemical crosslinking agent under conditions appropriate for the particular type of crosslinking reaction. For example, the osteoimplant of this invention can be immersed in a solution of cross-linking agent for a period of time sufficient to allow complete penetration of the solution into the osteoimplant. Crosslinking conditions include an appropriate pH and temperature, and times ranging from minutes to days, depending upon the level of crosslinking desired, and the activity of the chemical crosslinking agent. The resulting osteoimplant is then washed to remove all leachable traces of the chemical.

Suitable chemical crosslinking agents include mono- and dialdehydes, including glutaraldehyde and formaldehyde; polyepoxy compounds such as glycerol polyglycidyl ethers, polyethylene glycol diglycidyl ethers and other polyepoxy and diepoxy glycidyl ethers; tanning agents including polyvalent metallic oxides such as titanium dioxide, chromium dioxide, aluminum dioxide, zirconium salt, as well as organic tannins and other phenolic oxides derived from plants; chemicals for esterification or carboxyl groups followed by reaction with hydrazide to form activated acyl azide functionalities in the collagen; dicyclohexyl carbodiimide and its derivatives as well as other heterobifunctional crosslinking agents; hexamethylene diisocyante; sugars, including glucose, will also crosslink collagen.

Glutaraldehyde crosslinked biomaterials have a tendency to over-calcify in the body. In this situation, should it be deemed necessary, calcification-controlling agents can be used with aldehyde crosslinking agents. These calcification-controlling agents include dimethyl sulfoxide (DMSO), surfactants, diphosphonates, aminooleic acid, and metallic ions, for example ions of iron and aluminum. The concentrations of these calcification-controlling agents can be determined by routine experimentation by those skilled in the art.

When enzymatic treatment is employed, useful enzymes include those known in the art which are capable of catalyzing crosslinking reactions on proteins or peptides, preferably collagen molecules, e.g., transglutaminase as described in Jurgensen et al., *The Journal of Bone and Joint Surgery,* 79-a (2), 185–193 (1997), herein incorporated by reference.

Formation of chemical linkages can also be accomplished by the application of energy. One way to form chemical linkages by application of energy is to use methods known to form highly reactive oxygen ions generated from atmospheric gas, which in turn, promote oxygen crosslinks between surface-exposed collagen. Such methods include using energy in the form of ultraviolet light, microwave energy and the like. Another method utilizing the application of energy is a process known as dyemediated photo-oxidation in which a chemical dye under the action of visible light is used to crosslink surface-exposed collagen.

Another method for the formation of chemical linkages is by dehydrothermal treatment which uses combined heat and the slow removal of water, preferably under vacuum, to achieve crosslinking of bone particles. The process involves chemically combining a hydroxy group from a functional group of one collagen molecule and a hydrogen ion from a functional group of another collagen molecule reacting to form water which is then removed resulting in the formation of a bond between the collagen molecules.

The resulting osteoimplant can assume a determined or regular form or configuration such as a sheet, plate, disk, cone, pin, screw, tube, tooth, tooth root, bone or portion of bone, wedge or portion of wedge, cylinder, threaded cylinder (dowel), to name but a few. Of course, the osteoimplant can be machined or shaped by any suitable mechanical shaping means. Computerized modeling can, for example, be employed to provide an intricately-shaped osteoimplant which is custom-fitted to the bone repair site with great precision. In a preferred embodiment, the osteoimplant possesses the configuration of a threaded cylinder (dowel).

It will be understood that combinations of one or more of the foregoing operations can be employed, e.g., heating followed by lyophilizing; cross-linking followed by heating, etc.

The osteoimplant herein is applied at a bone repair site, e.g., one resulting from injury, defect brought about during the course of surgery, infection, malignancy or developmental malformation, which requires mechanical support. The osteoimplant can be utilized in a wide variety of orthopaedic, periodontal, neurosurgical and oral and maxillofacial surgical procedures such as the repair of simple and compound fractures and non-unions, external and internal fixations, joint reconstructions such as arthrodesis, general arthroplasty, cup arthroplasty of the hip, femoral and humeral head replacement, femoral head surface replacement and total joint replacement, repairs of the vertebral column including spinal fusion and internal fixation, tumor surgery, e.g., deficit filling, discectomy, laminectomy, excision of spinal cord tumors, anterior cervical and thoracic operations, repairs of spinal injuries, scoliosis, lordosis and kyphosis treatments, intermaxillary fixation of fractures, mentoplasty, temporomandibular joint replacement, alveolar ridge augmentation and reconstruction, onlay bone grafts, implant placement and revision, sinus lifts, etc. Specific bones which can be repaired or replaced with the bone-derived implant herein include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal and metatarsal bones. The osteoimplant can be implanted at the bone repair site, if desired, using any suitable affixation means, e.g., sutures, staples, bioadhesives, and the like.

Referring now to the drawings, FIGS. 1*a–h* depict various embodiments of an osteoimplant according to the present invention configured and dimensioned in the shape of a cylinder 40, wedge 50, plate 60, threaded cylinder (dowel) 70, fibular wedge 62, femoral struts 64, 66 and tibial strut 68. In accordance with a preferred embodiment, cylinder 20 and wedge 30 are provided with macroporosity, namely holes 42 and 52, respectively, which have been drilled into cylinder 40 and wedge 50. Macroporosity promotes blood flow through the osteoimplant and enhances and accelerates the incorporation of the osteoimplant by the host. Furthermore, macroporous holes 42 and 52 can be advantageously filled with an osteogenic material, e.g., Grafton® putty available from Osteotech, Inc., Eastontown, N.J.

Figure 1D:
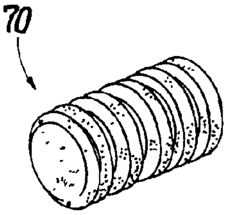
Figure 1E:
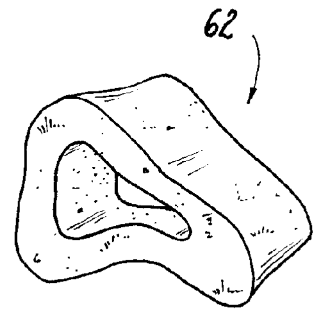
Figure 1F:
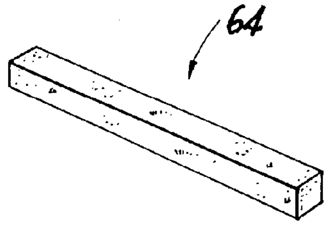
Figure 1G:
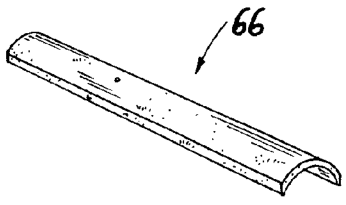
Figure 1H:
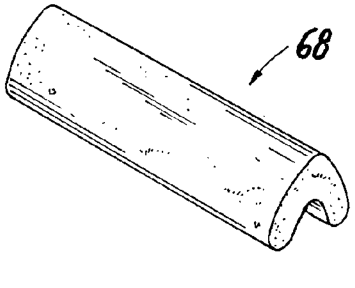
Figure 2A:
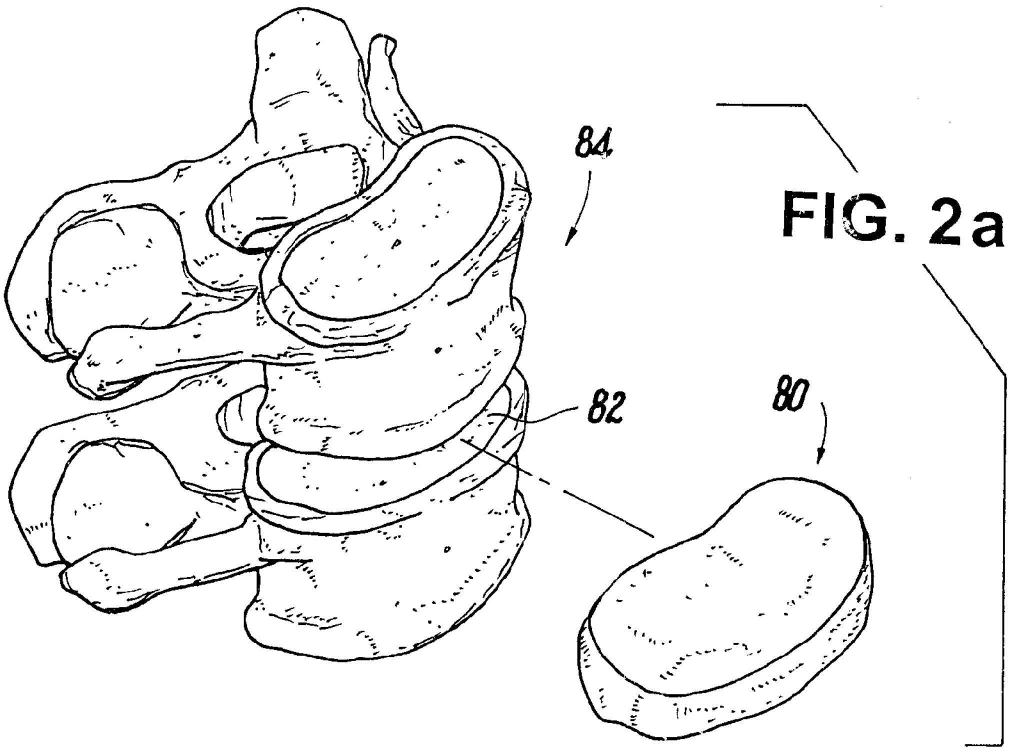
FIGS. 2*a* and 2*b* are views of a vertebrae and the osteoimplant of the invention sized and shaped as a disc (FIG. 2*a*) and threaded cylinder (FIG. 2*b*) for installation at an intervertebral site.
Figure 2B:
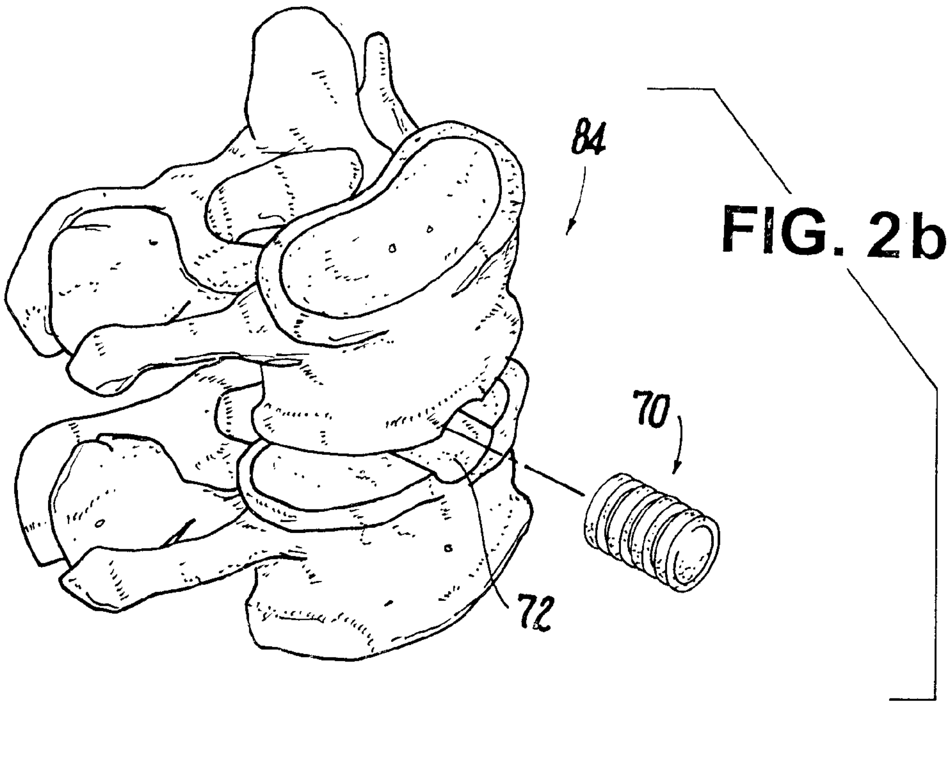

In FIG. 2*a,* osteoimplant 80 is configured and dimensioned as a disk to be inserted into the intervertebral fibrocartilage site 82 on the anterior side of vertebral column 84. In FIG. 2*b,* osteoimplant 70 is configured and dimensioned as a threaded cylinder (as depicted in FIG. 1*d*) to be inserted into the intervertebral site 72 on the anterior side of vertebral column 84.

Figure 3:
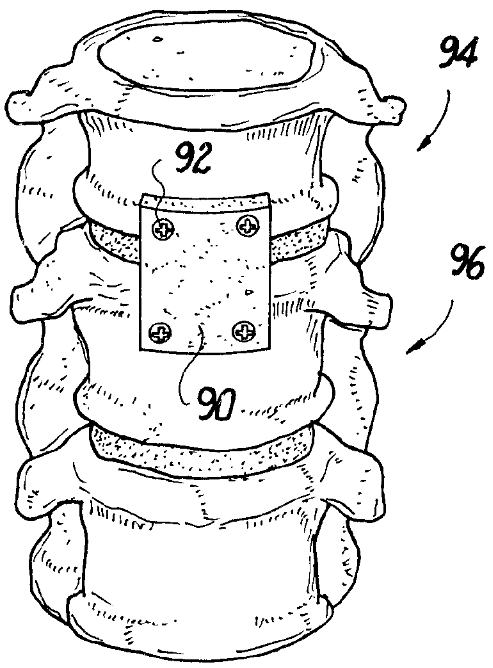
FIG. 3 is a view of human cervical vertebrae showing an osteoimplant of the invention affixed thereto as a cervical plate.

In FIG. 3, the osteoimplant of the invention is configured and dimensioned as a cervical plate 90 and is shown affixed to cervical vertebrae 94, 96 by bone screws 92. In accordance with a preferred embodiment, bone screws 92 form yet another embodiment of the osteoimplant of the present invention.

Figure 4:
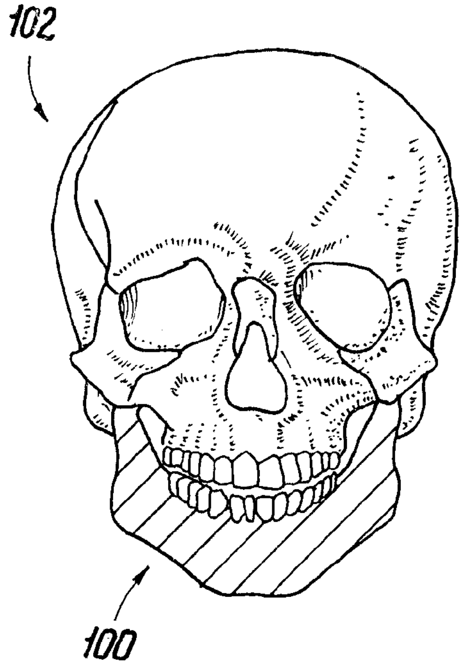
FIG. 4 is a view of the human skull showing an osteoimplant of the invention fashioned as a mandibular replacement.

In FIG. 4, the osteoimplant 100 of the invention is sized and shaped to form the mandible of skull 102.

Figure 5:
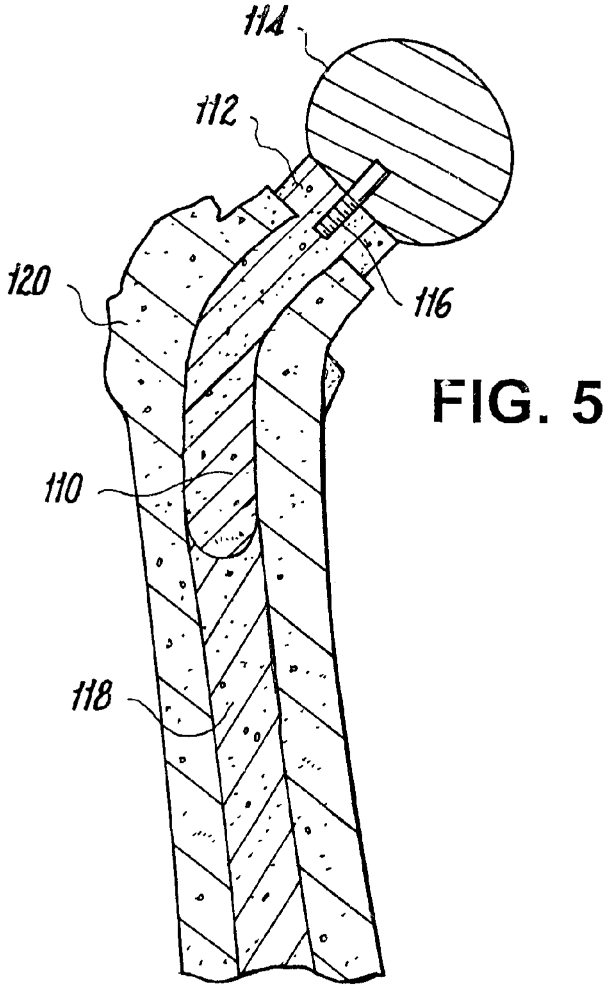
FIG. 5 is a cross-sectional view of a human femur showing implanted therein an osteoimplant fashioned as a femoral implant.

In FIG. 5, the osteoimplant 110 of the invention is sized and shaped as a femoral implant. Osteoimplant 110 comprises head 112 which is attached to ball 114. Ball 114 is fabricated from plastic or metal and is affixed to osteoimplant 110 by any suitable means, e.g, screw 116. Osteoimplant is inserted into intramedullary canal 118 of femur 120.

Figure 6A:
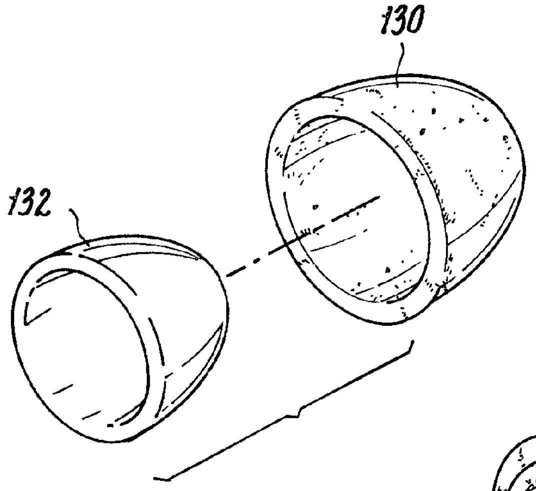
FIGS. 6*a* and 6*b* show an embodiment of the osteoimplant of the present invention configured and dimensioned as an acetabular cup.

In FIG. 6*a* and *b,* the osteoimplant 130 of the invention is sized and shaped as an acetabular cup which is configured and dimensioned to receive plastic or metallic liner 132.

Figure 6B:
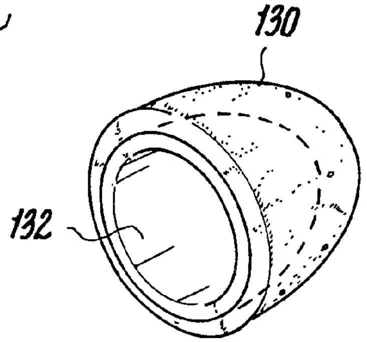
Figure 7:
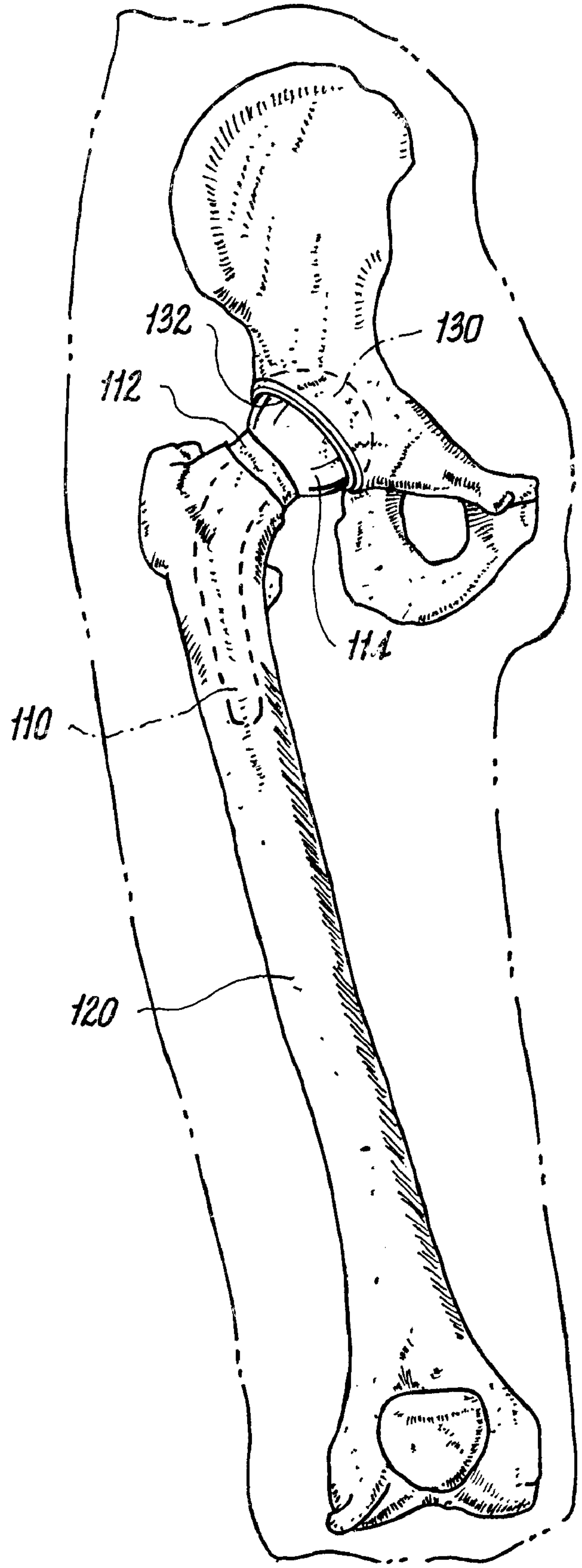
FIG. 7 is a view of a total hip replacement using the femoral implant depicted in FIG. 5 and the acetabular cup depicted in FIG. 6.

In FIG. 7, a total hip replacement with the osteoimplant 110 depicted in FIG. 5 and the osteoimplant 130 of FIGS. 6*a* and 6*b* is depicted.

Figure 8A:
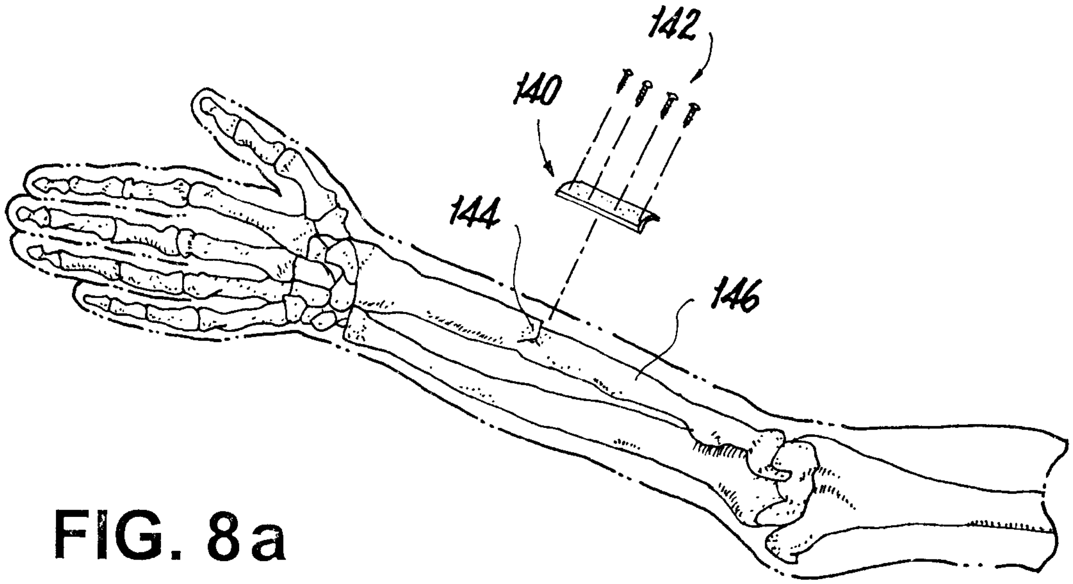
FIGS. 8*a* and 8*b* are views of a human radius and ulna showing an osteoimplant of the invention fashioned as a diaphyseal plate being implanted at a bone fracture site (FIG. 8*a*) and as an intercalary implant implanted at a diaphyseal segment missing due to trauma or tumor (FIG. 8*b*)

In FIG. 8*a,* the osteoimplant 140 of the invention is sized and shaped as a diaphyseal implant and is shown being implanted via bone screws 142 on a fracture 144 along the diaphyseal segment of a human radius 146. Optionally, and preferably, screws 142 can be fabricated from compressed bone particles in accordance with this disclosure.

Figure 8B:
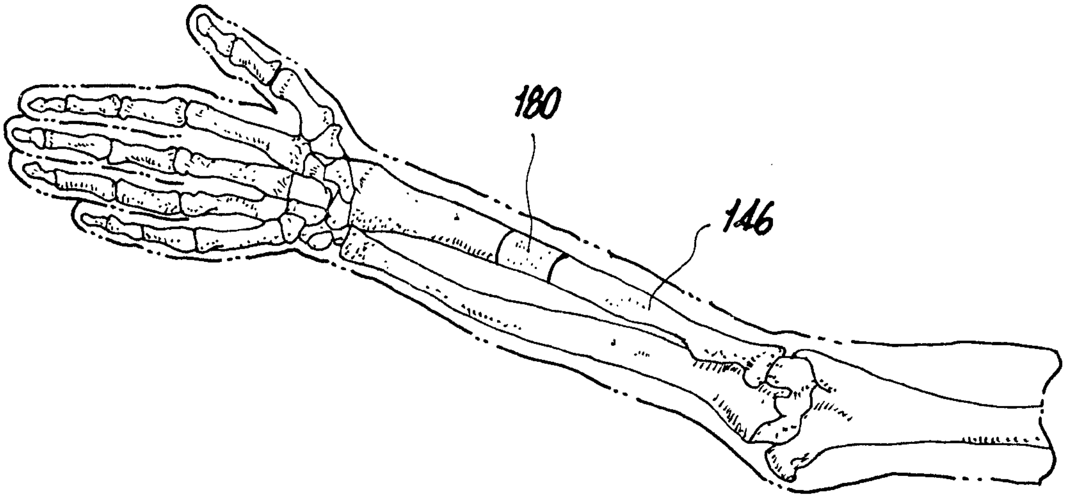

In FIG. 8*b,* osteoimplant 180 of the invention is sized and shaped as an intercalary implant and is shown already implanted at a diaphyseal segment of human radius 146 that is missing due to trauma or tumor.

Figure 9:
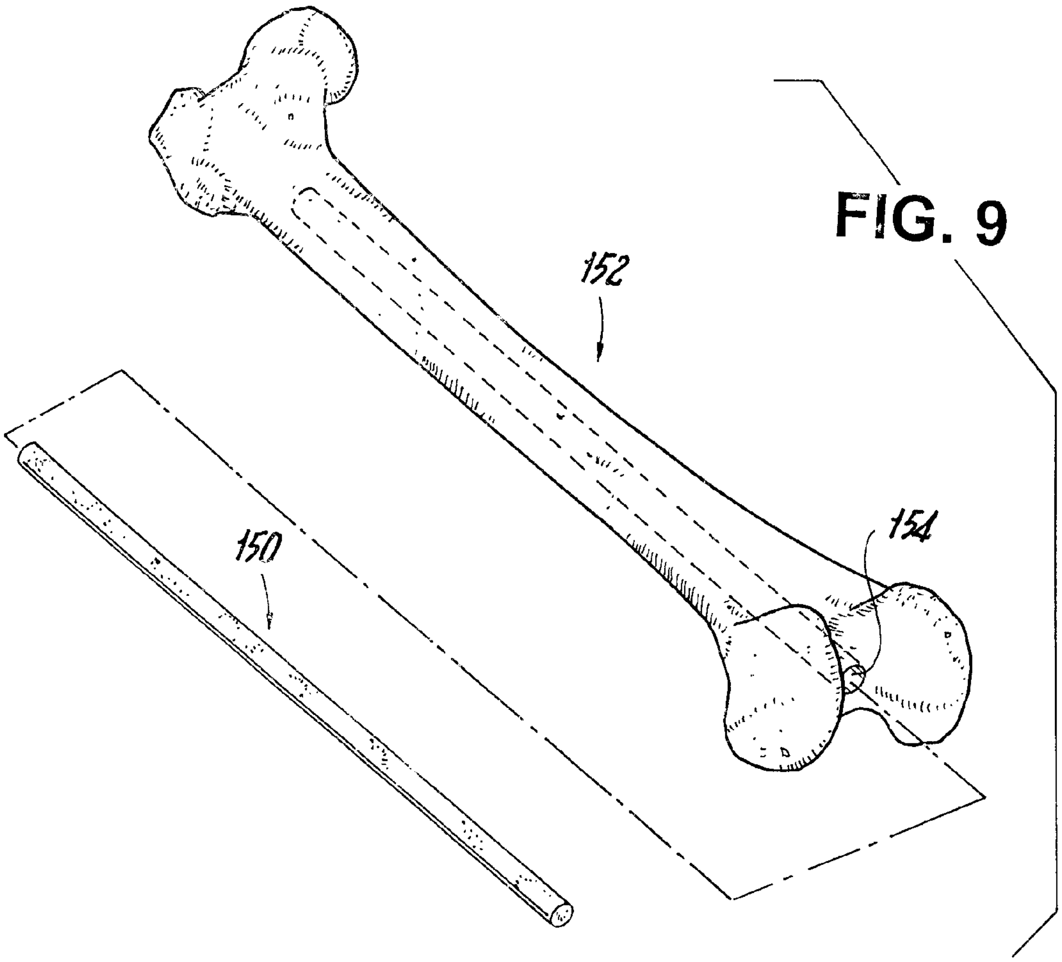
FIG. 9 is a view of a human femur and an osteoimplant of the invention fashioned as an intramedullary rod positioned for installation in the medullary canal of the femur.

In FIG. 9, the osteoimplant 150 of the invention is sized and shaped as an intramedullary rod for insertion into the medullary canal 154 of femur 152.

Figure 10:
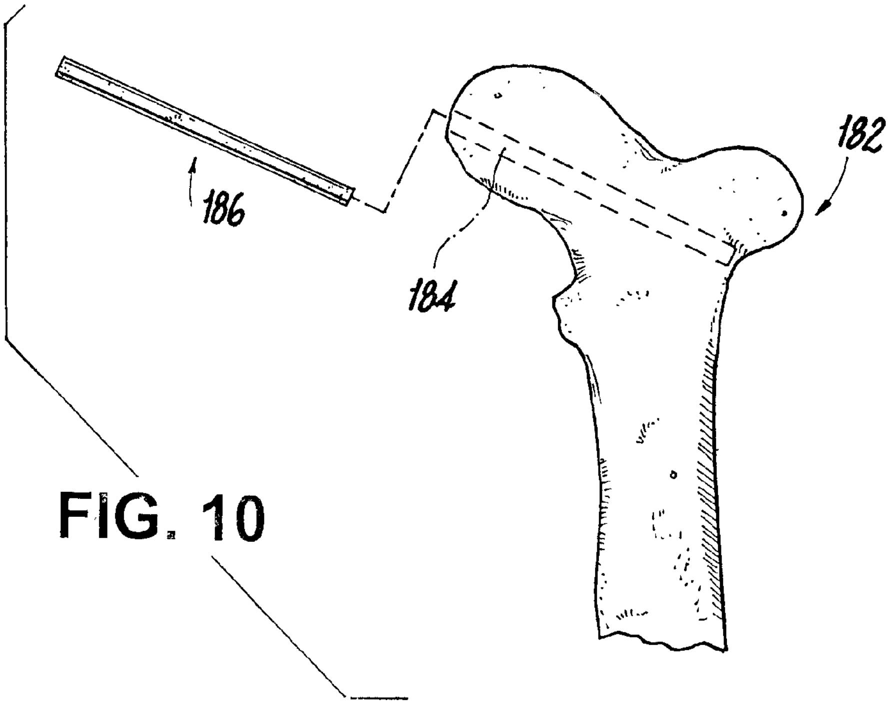
FIG. 10 is a view of a femoral head and an osteoimplant of the invention positioned for installation in a core decompression site in the femoral head.

In FIG. 10, osteoimplant 186 is sized and shaped as a reinforcement rod for insertion into a core decompression site 184 formed by drilling a hole into femoral head 182.

Figure 11:
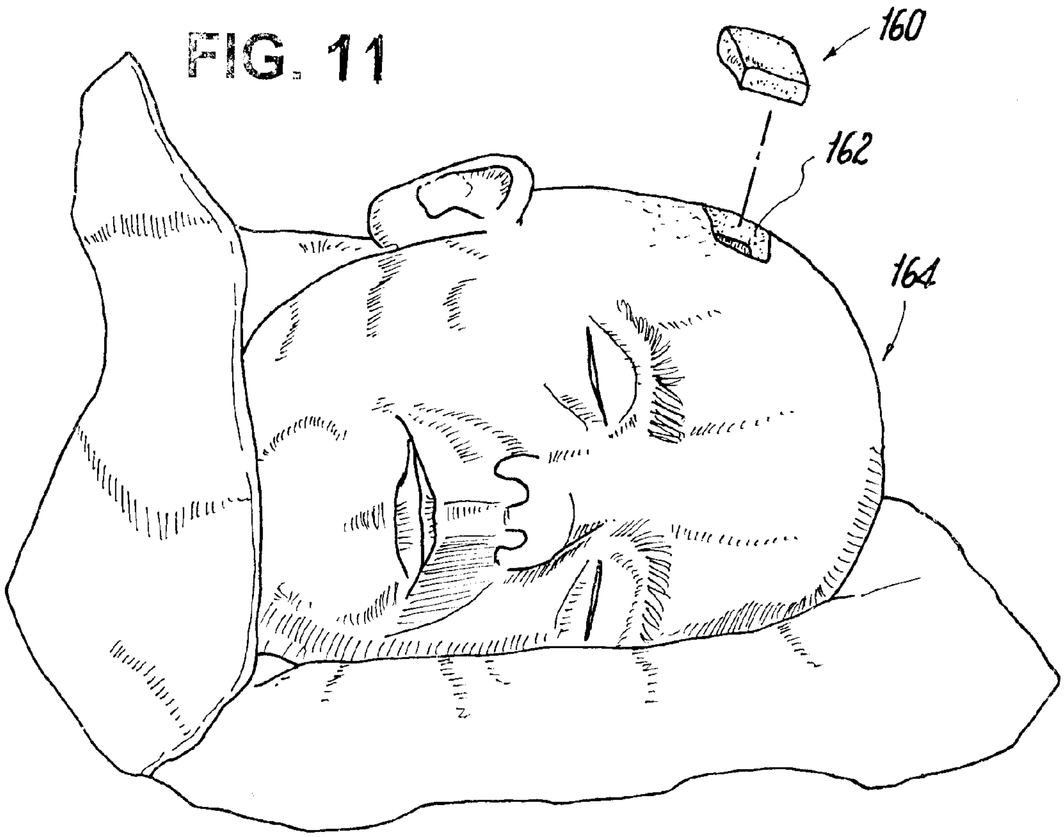
FIG. 11 is a view of a human skull and an osteoimplant of the present invention positioned for implantation as a parietal bone replacement.

In FIG. 11, osteoimplant 160 is sized and shaped to form part of the parietal bone 162 for skull 164. Osteoimplant 160 promotes fusion with parietal bone 88.

The present invention is intended to embrace all such devices which are constructed as the osteoimplant of the present invention and the attendant uses of such devices.

It will also be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The following examples illustrate the practice of this invention.

Wet Compressive Strength

Wet compressive strength of the osteoimplant of this invention is measured using the following method:

Initial density is determined by measuring specimen dimensions with a caliper to determine volume, and then weighing the specimen on a laboratory balance. The specimen is then placed in a container with 0.9% NaCl solution at room temperature for 12–24 hours. After the hydration period, the specimen is measured again to determine dimensions, and dimensions are recorded. The specimen is then centered on a compression platen (MTS 643.10A-01) in a servohydraulic testing system (MTS 858 Bionix). The top platen is lowered onto the specimen until a compressive preload of 0.1 kN is achieved. The system displacement transducer is then zeroed (MTS 358.10), defining zero displacement as the displacement associated initially with 0.1 kN preload. Using system software (MTS 790.90 Testworks for Teststar), the specimen is loaded in the displacement mode, using a ramp compressive load of 0.5 mm/s, until an endpoint of 4 mm displacement is achieved. After the 4 mm displacement is achieved, the loading is stopped automatically, and the specimen is unloaded. During testing, load (from the system load cell MTS 661.20E-03) and displacement data are collected every 0.05 sec.

EXAMPLE 1

Elongate bone particles were prepared using a milling machine. Half of the volume of the particles was fully demineralized using two charges of 0.6N HCl acid. The nondemineralized and the fully demineralized particles were then combined together in an aqueous solution containing glycerol and allowed to soak for 4–12 hours at room temperature. The particles were then removed from the solution by straining, and placed into a 28 mm diameter cylindrical press-mold while still moist. The particles were pressed to 10,000 psi for 15 minutes. The resulting compressed pellet was heated in situ in an oven for 4 hours at 45° C. The osteoimplant was then frozen in a −70° C. freezer (1.5 hours), and freeze-dried overnight, after which it was removed from the mold. The bulk density of the osteoimplant produced was 1.34 $g/cm^3$. The height of the osteoimplant was 29 mm. The wet compressive strength of the osteoimplant exceeded 3 MPa.

EXAMPLE 2

The procedure of Example 1 was used except the ratio of fully demineralized to nondemineralized bone particles was 2:1, the pellet was heated in situ in an oven for 4 hours at 40° C. and the pressure was 2,500 psi. The resulting compressed pellet was cut into two portions and each portion was treated with crosslinking agent: 10% neutral buffered formalin (both dipped and in vapor phase) and 4% Denacol EX313 (a polyepoxy-ether compound available from Nagase America Corp., New York, N.Y.), respectively. In each case, the resulting osteoimplant swelled a little and became stiff, and resistant to manual pressure. The bulk density of the osteoimplant produced was 1.2 $g/cm^3$. The wet compressive strength of the osteoimplant exceeded 3 MPa.

EXAMPLE 3

The procedure of Example 1 was followed except that all of the particles were partially demineralized by using 225 ml of 0.6N HCl and allowing the acid to react to depletion. Additionally, the mold was hexagonal in configuration (with each side of the hexagon measuring 18 mm). After completing the freeze-drying step, the resulting osteoimplant was placed in a bath of 10% neutral buffered formalin and the exposed collagen of the partially demineralized bone particles was allowed to cross-link for 48 hours. The resulting dry osteoimplant was tested mechanically and was found to possess a dry compressive strength of about 85 MPa. The bulk density of the osteoimplant was 1.05 g/$cm^3$.

EXAMPLE 4

The procedure of Example 3 was repeated and the resulting osteoimplant was immersed in physiological saline for 12–24 hours and was found to possess an ultimate wet compressive strength of about 45 MPa. The bulk density of the osteoimplant was 1.05 g/$cm^3$.

EXAMPLE 5

Elongate bone particles were prepared using a milling machine. The nondemineralized particles were then combined with ethyl cellulose (3:2 ratio by weight), and covered with 70% ethanol for 30 minutes, with stirring. The elongate bone particles were then removed from the solution by straining, and placed into a press-mold while still moist. The elongate bone particles were pressed to 10,000 psi for 15 minutes. The resulting compressed pellet was heated in situ in an oven for 4 hours at 45° C. The implant was then frozen in a −70° C. freezer (overnight), and freeze-dried, after which it was removed from the mold. The osteoimplant was immersed in physiological saline overnight and was found to possess a wet compressive strength of 20 MPa.

EXAMPLE 6

Bone particles were prepared by using a block plane on the periosteal surface of cortical bone. Half of the volume of the bone particles was fully demineralized using two changes of 0.6N HCl acid. The mineralized (25 g) and the demineralized particles (25 g based on original weight) were then combined together in a 70% ethanol solution with 20 g ethyl cellulose. This mixture was stirred for 30 minutes at room temperature. The particles were then removed form the solution by straining, and placed into a cylindrical press-mold while still moist. The particles were pressed to 18,000 psi for 10 minutes. The resulting compressed pellet was heated in situ in an oven for 4 hours at 45° C. The implant was then frozen in a −70° C. freezer (1.5 hours), and freeze-dried overnight, after which it was removed from the mold. The dry compressive strength of the osteoimplant was 6.5 MPa and the wet compressive strength of the osteoimplant was 4.0 MPa.

EXAMPLE 7

Elongate bone particles were prepared using a milling machine (30 g). An equivalent amount by weight of cortical bone chips were also prepared by grinding in a bone mill. Chips were sieved between screens having dimensions between 4.0 mm and 1.8 mm. The elongate particles and the chips were then combined together in a container with 70% Ethanol (1 liter) and ethyl cellulose (20 g). The components were mixed together thoroughly and allowed to soak for 30 minutes at room temperature. The mixture was then removed from the excess solution by straining, and placed into a pressmold while still moist. The particles were pressed to 10,000 psi for 10 minutes. The resulting compressed pellet was heated in situ in an oven for 4 hours at 45° C. The implant was then frozen in a −70° C. freezer (1.5 hours), and freeze-dried overnight, after which it was removed from the mold. The wet compressive strength of the osteoimplant exceeded 3 MPa.

EXAMPLE 8

Twenty grams of elongate bone particles were produced by milling from diaphyseal bone. The nondemineralized elongate bone particles were mixed with 10 grams dry ethyl cellulose. To this mixture, 150 ml of 95% ethanol was added, and the mixture was stirred for 30 minutes. The fluid was then drained off, and 20 ml of elongate bone particles was measured out and placed in a cylindrical press-mold. The elongate bone particles were pressed for 10 minutes at 56,000 psi. After pressing, the pellet, still in its mold, was placed in an oven at 45° C. for 4 hours, and then in a −70° C. freezer overnight. The pellet was freeze-dried for about 3 days. The resulting osteoimplant (10 mm dia. by 9.1 mm high cylinder) was then re-hydrated overnight in physiological saline (water containing 0.9 g NaCl/100 ml water). The wet compressive strength of the osteoimplant was 31.9 MPa.

EXAMPLE 9

Elongate bone particles were produced by milling from diaphyseal bone. These elongate bone particles were then partially demineralized using 14 ml of 0.6 HCl acid solution. The acid was allowed to react to exhaustion (pH~7). The partially demineralized elongate bone particles were then washed in water, and placed into a 13 mm cylindrical press-mold. The filled mold was placed in a heated water bath made by surrounding an open-topped metal flask with a heating strip. The water was heated continuously to 70° C. during the pressing process. The bone particles were pressed at 120,000 psi for 3 days. The pellet produced was placed in a −70° C. freezer for 1 hour, then freeze-dried for 24 hours. The resulting osteoimplant had a bulk density of 1.9 g/$cm^3$. This osteoimplant was rehydrated overnight in physiological saline, and then tested for wet compressive strength. The resulting wet compressive strength was 56.4 MPa.

EXAMPLE 10

An osteoimplant was prepared as in Example 9, except that the bone particles used were 100–500 μm powder, superficially demineralized with 0.6N HCl. The mold size was 10 mm diameter for this example. The resulting osteoimplant had a bulk density of 1.9 g/$cm^3$ and a wet compressive strength of 17.6 MPa.

EXAMPLE 11

An osteoimplant was prepared as in Example 9, except that the elongate bone particles were pressed in a 10 mm diameter mold for 24 hours at 40° C. The resulting osteoimplant had a bulk density of 1.8 g/$cm^3$, and a wet compressive strength of 41.6 MPa.

EXAMPLE 12

An osteoimplant was prepared as in Example 9, except that the elongate bone particles were placed in a 50% aqueous solution of glycerol and were pressed in a 10 mm diameter mold surrounded by heated 50% aqueous solution of glycerol at 40° C. The implant was pressed to 40,000 psi for 24 hours. The resulting osteoimplant had a bulk density of 1.6 g/$cm^3$, and a wet compressive strength of 12.5 MPa.

What is claimed is:

1. An intervertebral implant which comprises a shaped composition of bone particles, wherein the composition possesses a bulk density of greater than about 0.7 g/$cm^3$ and a wet compressive strength of at least about 3 MPa.

2. A spinal implant which comprises a shaped composition of bone particles, wherein the composition possesses a bulk density of greater than about 0.7 g/$cm^3$ and a wet compressive strength of at least about 3 MPa.

3. An implant possessing the shape of a cylinder, wedge, plate, threaded cylinder, fibular wedge, femoral strut or tibial strut which comprises a shaped composition of bone particles, wherein the composition possesses a bulk density of greater than about 0.7 g/cm$^3$ and a wet compressive strength of at least about 3 MPa.

4. The osteoimplant of claim 3 further comprising at least one macroporous hole.

5. The osteoimplant of claim 4 wherein the macroporous hole contains therein an osteogenic material.

6. A bone plate which comprises a shaped composition of bone particles, wherein the composition possesses a bulk density of greater than about 0.7 g/cm$^3$ and a wet compressive strength of at least about 3 MPa.

7. A disk which comprises a shaped composition of bone particles, wherein the composition possesses a bulk density of greater than about 0.7 g/cm$^3$ and a wet compressive strength of at least about 3 MPa.

8. A bone screw which comprises a shaped composition of bone particles, wherein the composition possesses a bulk density of greater than about 0.7 g/cm$^3$ and a wet compressive strength of at least about 3 MPa.

9. A femoral implant which comprises a shaped composition of bone particles, wherein the composition possesses a bulk density of greater than about 0.7 g/cm$^3$ and a wet compressive strength of at least about 3 MPa.

10. An acetablular cup implant which comprises a shaped composition of bone particles, wherein the composition possesses a bulk density of greater than about 0.7 g/cm$^3$ and a wet compressive strength of at least about 3 MPa.

11. A diaphyseal implant which comprises a shaped composition of bone particles, wherein the composition possesses a bulk density of greater than about 0.7 g/cm$^3$ and a wet compressive strength of at least about 3 MPa.

12. An intercalary implant which comprises a shaped composition of bone particles, wherein the composition possesses a bulk density of greater than about 0.7 g/cm$^3$ and a wet compressive strength of at least about 3 MPa.

13. An intramedullary implant which comprises a shaped composition of bone particles, wherein the composition possesses a bulk density of greater than about 0.7 g/cm$^3$ and a wet compressive strength of at least about 3 MPa.

14. A reinforcement rod implant which comprises a shaped composition of bone particles, wherein the composition possesses a bulk density of greater than about 0.7 g/cm$^3$ and a wet compressive strength of at least about 3 MPa.

15. A cranial bone implant which comprises a shaped composition of bone particles, wherein the composition possesses a bulk density of greater than about 0.7 g/cm$^3$ and a wet compressive strength of at least about 3 MPa.

16. A maxillofacial implant which comprises a shaped composition of bone particles, wherein the composition possesses a bulk density of greater than about 0.7 g/cm$^3$ and a wet compressive strength of at least about 3 MPa.

17. A method of repairing bone comprising implanting at a bone repair site the load-bearing osteoimplant of claim 1 comprising a shaped composition of bone particles, said osteoimplant possessing a bulk density of greater than about 0.7 g/cm$^3$ and a wet compressive strength of at least 3 MPa.

18. The method of repairing bone of claim 17 selected from the group consisting of the repair of simple and compound fractures and non-unions, external and internal fixations, joint reconstructions, arthrodesis, general arthroplasty, cup arthroplasty of the hip, femoral and humeral head replacement, femoral head surface replacement and total joint replacement, repairs of the vertebral column, spinal fusion, internal fixation, tumor surgery, deficit filling, discectomy, laminectomy, excision of spinal cord tumors, anterior cervical and thoracic operations, repairs of spinal injuries, scoliosis, lordosis and kyphosis treatments, intermaxillary fixation of fractures, mentoplasty, temporomandibular joint replacement, alveolar ridge augmentation and reconstruction, onlay bone grafts, implant placement and revision, and sinus lifts.

19. An osteoimplant comprising a shaped, compressed composition of demineralized bone particles possessing chemical crosslinking of the surface-exposed collagen thereof, the osteoimplant possessing a bulk density of greater than about 0.7 g/cm$^3$ and a wet compressive strength of at least about 3 MPa.

20. The osteoimplant of claim 19 wherein the demineralized bone particles are selected from the group consisting of superficially demineralized bone particles, partially demineralized bone particles and substantially fully demineralized bone particles.

21. The osteoimplant of claim 19 wherein the bone particles are obtained from cortical, cancellous or corticocancellous bone of autogenous, allogenic or xenogeneic origin.

22. The osteoimplant of claim 19 wherein the bone particles are obtained from porcine or bovine bone.

23. The osteoimplant of claim 19 further comprising nondemineralized bone particles.

24. The osteoimplant of claim 19 wherein at least about 60 weight percent of the bone particles are elongate.

25. The osteoimplant of claim 19 wherein at least about 90 weight percent of the bone particles are elongate.

26. The osteoimplant of claim 19 further comprising at least one biocompatible component.

27. The osteoimplant of claim 26 wherein the biocompatible component is selected from the group consisting of biocompatible adhesive, binder, filler, fiber and bioactive substance.

28. The osteoimplant of claim 27 wherein the bioactive substance is selected from the group consisting of collagen, insoluble collagen derivatives, and soluble solids and/or liquids dissolved therein; antiviricides, antimicrobials and/or antibiotics selected from the group consisting of erythromycin, bacitracin, neomycin, penicillin, polymycin B. tetracyclines, biomycin, ehloromycetin, streptomycins, cefaxolin, ampicillin, azactam, tobramycin, clindamycin and gentamicin; biocidal/biostatic sugars selected from the group consisting of dextran, glucose, amino acids, peptides; vitamins; inorganic elements; co-factors for protein synthesis; hormones; endocrine tissue or tissue fragments; synthesizers; enzymes selected from the group consisting of collagenase, peptidases, oxidases; polymer cell scaffolds with parenchymal cells; angiogenic drugs and polymeric carriers containing such drugs; collagen lattices; antigenic agents; cytoskeletal agents; cartilage fragments; living cells selected from the group consisting of chondrocytes, bone marrow cells, mesenchymal stem cells, natural extracts, genetically engineered living cells or otherwise modified living cells, DNA delivered by plasmid or viral vectors, and tissue transplants; demineralized bone powder; autogenous tissues selected from the group consisting of blood, serum, soft tissue, bone marrow, bioadhesives, bone morphogenic proteins (BMPs); osteoinductive factor (IFO); fibronectin (FN); endothelial cell growth factor (ECGF); cementum attachment extracts (CAE); ketanserin; human growth hormone (HGH); animal growth hormones; epidermal growth factor (ECF); interleukin-1 (IL-1); human alpha thrombin; transforming growth factor (TGF-beta); insulin-like growth factor (IGF-1); platelet derived growth factors (PDGF); fibroblast growth factors (FGF, bFGF, etc.); periodontal ligament chemotactic factor (PDLGF); somatotropin; bone digestors; antitumor agents; immuno-suppressants; permeation enhancers; enamine derivatives; alpha-keto aldehydes; and nucleic acids.

29. The osteoimplant of claim 23 wherein the weight ratio of nondemineralized bone particles to demineralized bone particles ranges from about 20:1 to about 1:20.

30. The osteoimplant of claim 23 wherein the weight ratio of partially demineralized bone particles to fully demineralized bone particles ranges from about 20:1 to about 1:20.

* * * * *